(12) United States Patent
Rochat

(10) Patent No.: US 6,820,620 B2
(45) Date of Patent: Nov. 23, 2004

(54) RESPIRATORY ASSISTANCE APPARATUS

(76) Inventor: Jean-Denis Rochat, En Tenet, CH 1272 Genolier (CH)

( * ) Notice: Subject to any disclaimer, the term of this patent is extended or adjusted under 35 U.S.C. 154(b) by 0 days.

(21) Appl. No.: 10/464,194

(22) Filed: Jun. 18, 2003

(65) Prior Publication Data

US 2004/0035425 A1 Feb. 26, 2004

Related U.S. Application Data

(63) Continuation of application No. PCT/IB01/02627, filed on Dec. 20, 2001.

(51) Int. Cl.[7] .................................................. A62B 9/02
(52) U.S. Cl. .............................. 128/205.24; 128/205.14
(58) Field of Search ....................... 128/205.24, 205.14; 137/487.5; 251/129.07, 129.17

(56) References Cited

U.S. PATENT DOCUMENTS

| 321,426 | A | * | 7/1885 | Ells ......................... 137/487.5 |
| 763,054 | A | * | 6/1904 | Gamble .................. 251/129.16 |
| 1,197,860 | A | * | 9/1916 | Schneider .................... 137/495 |
| 2,047,734 | A | * | 7/1936 | Hetzer ....................... 137/102 |
| 2,050,430 | A | * | 8/1936 | Erickson ................ 137/614.19 |
| 2,299,404 | A | * | 10/1942 | Newton .................... 137/487.5 |
| 2,412,490 | A | * | 12/1946 | Biggle .................... 137/505.12 |
| 2,646,932 | A | * | 7/1953 | Frost ....................... 236/80 R |
| 3,861,412 | A | * | 1/1975 | Fleischmann ................ 137/83 |
| 3,863,082 | A | * | 1/1975 | Gillott et al. .................. 310/27 |
| 3,972,327 | A | * | 8/1976 | Ernst et al. ............ 128/204.21 |
| 4,224,940 | A | * | 9/1980 | Monnier ................. 128/205.16 |
| 4,495,947 | A | * | 1/1985 | Motycka ................. 128/205.14 |
| 4,595,004 | A | * | 6/1986 | Czech .................... 128/204.21 |
| 4,838,257 | A | * | 6/1989 | Hatch .................... 128/204.18 |
| 5,063,925 | A | * | 11/1991 | Frank et al. ........... 128/205.24 |
| 5,065,746 | A | * | 11/1991 | Steen .................... 128/205.24 |
| 5,127,400 | A | * | 7/1992 | DeVries et al. ........ 128/205.24 |
| 5,507,282 | A | * | 4/1996 | Younes .................. 128/204.21 |
| 5,884,623 | A | * | 3/1999 | Winter .................. 128/205.24 |
| 6,247,493 | B1 | * | 6/2001 | Henderson ............... 137/487.5 |

FOREIGN PATENT DOCUMENTS

| EP | 0217573 | 4/1987 |
| FR | 1525881 | 5/1968 |
| FR | 2733688 | 11/1996 |
| WO | WO 95 31241 | 11/1995 |

* cited by examiner

Primary Examiner—Aaron J. Lewis
(74) Attorney, Agent, or Firm—Sturm & Fix LLP

(57) ABSTRACT

The invention concerns a method for open-loop regulation of a breathing aid apparatus which consists in constituting a compression chamber by dividing it into two compartments each connected to an intake of air or breathing mixture and to an outlet of compressed air, using an elastic floating diaphragm guiding said floating diaphragm by fixing its periphery to the wall of said chamber fixing a field coil at the center of said floating diaphragm, placing said field coil in an air gap which is oriented in the direction deforming said floating diaphragm, measuring the instantaneous flow rate of air leaving through said outlet and powering said field coil continuously calculating the instantaneous intensity and the direction of the supply current on the basis of the set pressure of compressed air, of said instantaneous flow rate and of the constants of said apparatus.

17 Claims, 2 Drawing Sheets

RESPIRATORY ASSISTANCE APPARATUS

CROSS REFERENCE TO RELATED APPLICATIONS

This application is a Continuation application of PCT/IB01/02627 filed Dec. 20, 2001, claiming priority of European Application No. 00811237.7 filed Dec. 22, 2000, which are included in their entirety by reference made hereto.

BACKGROUND OF THE INVENTION

1. Field of the Invention

The present invention relates to an open loop pressure regulation method for a respiratory assistance apparatus, and to a compression device of a compression apparatus for implementing this method.

2. Description of the Related Art

The problem encountered with respiratory assistance apparatuses which are required to supply a variable air flow rate at constant pressure is that of the response time. It is in fact necessary to succeed in producing an endotracheal reference pressure which can be adjusted by the practitioner, which is independent of the instantaneous inhalation flow rate demanded by the patient, the exhalation passing through an exhalation valve, the inhalation valve then being closed.

There are two types of respiratory assistance apparatuses. The apparatuses of the first type comprise a pressurized respiratory gas supply, the flow rate and the pressure of which are regulated by a regulating valve with a variable constriction. The apparatuses of the second type have no pressurized gas supply, but a compressor with variable pressure and flow rates.

Existing apparatuses operate with pressure feedback, which requires a compromise between stability of the closed-loop system and its response time. The response time of such systems is about 50 to 150 ms, while the response time of the valve is about 4 to 10 ms.

It would not be possible to operate in open-loop mode with such a system, given the friction which is not a fixed parameter and the measurement of which would be too complex. To operate in open-loop mode, it is therefore first of all essential to find a compression device operating virtually without mechanical friction. FR-2733688 has already proposed a respiratory assistance apparatus whose pressurized gas source is a compressor with an electromagnetically actuated membrane. This compressor comprises a casing which contains two chambers of variable volume having a guide shaft which passes through a soft iron core placed coaxially at the center of an annular magnet and which bears at each of its ends a rigid circular plate fitted with an annular membrane, the periphery of which is fastened to the inner wall of the casing, thus defining, inside the casing, two chambers, the respective volumes of which vary according to the displacement of the plates and membranes. Each chamber comprises at least one inlet valve and at least outlet valve in order to control the inlet and outlet of the air.

Such a compression device does not meet the requirements of a system operating in open-loop mode, given that the guide shaft is a significant source of friction.

BRIEF SUMMARY OF THE INVENTION

The aim of the present invention is to make it possible to provide a solution to regulating a respirator comprising a membrane compressor, so that its response time is reduced virtually to that of the membrane of the compression device.

To this end, the subject of the present invention is first of all a method of regulating, in open-loop mode, a respiratory assistance apparatus, as claimed claim 1. The subject of the invention is also a respiratory assistance apparatus as claimed in claim 3.

The advantage of this method and of the apparatus for its implementation arises from the fact that in the absence of mechanical friction, it is enough to measure the flow rate and to know the reference pressure in order to calculate the instantaneous supply current of the driving coil, the other parameters consisting of the constants of the respiratory assistance apparatus.

The appended drawing illustrates, schematically and by way of example, one embodiment of the respiratory assistance apparatus for implementing the method which is the subject of the present invention.

DETAILED DESCRIPTION OF THE INVENTION

Figure 1:
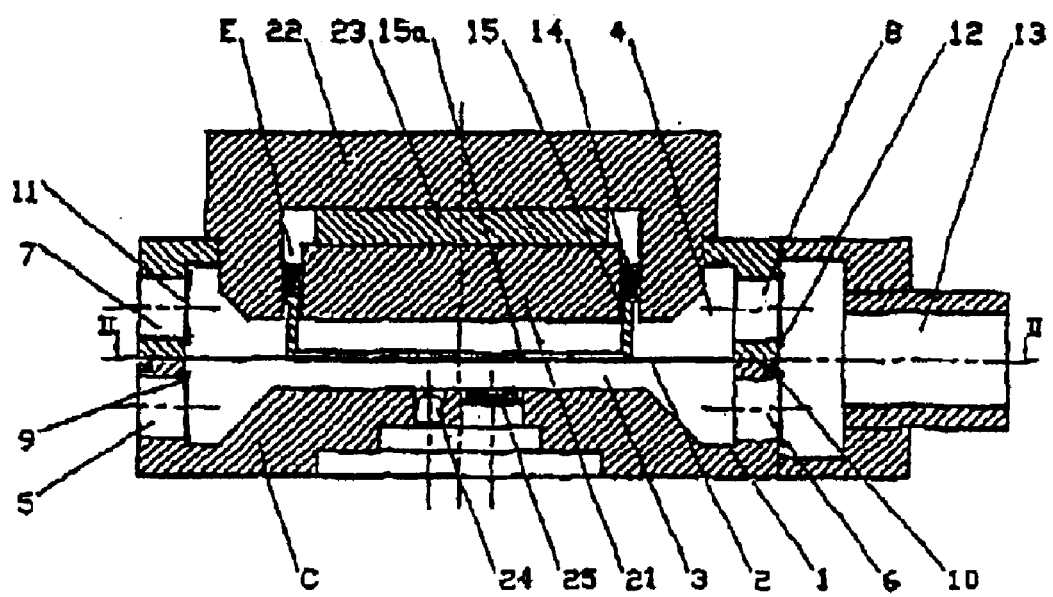
FIG. 1 is a view in axial section of the compression device which is the subject of the present invention.
Figure 2:
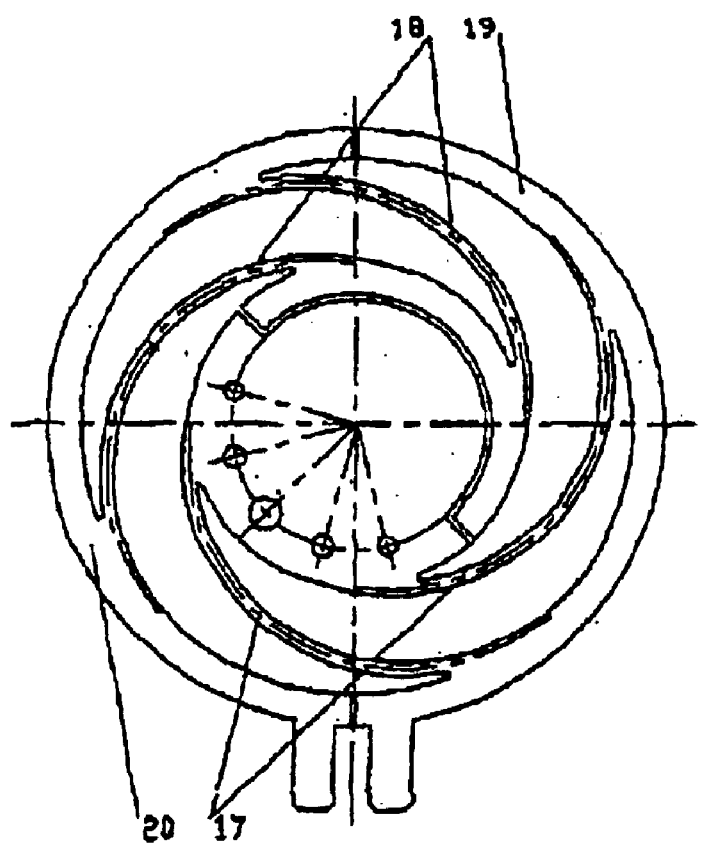
FIG. 2 is a view along II—II of FIG. 1.

To make it possible to implement the regulation method according to the invention, a compression device as illustrated in FIG. 1 is produced which comprises a casing C, inside which is made a compression chamber 1 divided into two compartments 3 and 4 by a floating elastic membrane 2 made of silicone, the periphery of which is fastened to the wall of this chamber 1. This floating membrane 2 provides the seal between the two compartments. This membrane 2 is called floating since it is entirely guided by the fastening of its periphery to the wall of the chamber 1, to the exclusion of any other guiding generating mechanical friction constituting a significant and essentially variable parameter which does not allow regulation in open-loop mode.

Preferably, this floating membrane 2 is subject to some pre-tension when it is fastened to the wall of the chamber 1. To this end, the membrane is stretched diametrally by 3 to 8%, preferably 4 to 5%. The aim of this pre-tension is to limit the dead flutter of the membrane when the pressure exerted thereon is unused.

Each compartment 3, 4 communicates with the outside by two openings 5, 6 or 7, 8, respectively. Preferably, each compartment comprises a plurality of inlet and outlet valves. Each of these openings 5–8 is controlled by a nonreturn valve 9 to 12, respectively. The two valves 9, 10 or 11, 12 of each compartment 3, 4 respectively operate inversely to each other, such that the valves 9 and 11 allow air to enter the respective compartments 3, 4 but prevents it from leaving, while the valves 10 and 12 allow the air to leave these same compartments 3, 4 but not to enter them.

The intake openings 5, 7 communicate with the atmosphere, while the openings 6 and 8 open out into an outlet duct 13 intended to take the pressurized air into the patient's trachea.

The floating membrane 2, preferably of circular shape, bears a cylindrical driving coil 14. This driving coil 14 is wound on a plastic hollow cylinder 15, (FIG. 1), the bottom 15a of which is secured to the floating membrane 2. Two arcuate springy arms 17, 18, made of a Cu—Be alloy, respectively, connect two copper half-disks 16a, 16b, placed between the bottom 15a of the hollow cylinder 15 and the floating membrane 2, to two half-rings 19, 20. As a variant, each of these arcuate arms 17, 18 could also be divided into several parallel arms. These two springy arms 17, 18 are symmetrical with respect to the center of the floating membrane 2. The two half-rings 19, 20 are fastened between two parts of the casing C and are connected to the two respective poles of a current source I for supplying the driving coil 14.

These two arms 17, 18 also serve to center the moving element formed by the floating membrane 2 and the driving coil 14 and to guide this element during its displacement.

This driving coil 14 is placed in a gap E made between a soft iron core 21 and a soft iron yoke 22 which are connected respectively to the two poles of a permanent magnet 23 forming an electrodynamic motor where the magnetic force is essentially independent of the coil position.

The compression device also comprises a light-emitting diode 24 placed opposite a reflecting surface borne by the floating membrane 2 and a photodiode 25 intended to pick up the light reflected by the reflecting surface, depending on the position of the floating membrane 2, whose displacement is induced by the driving coil 14 as a function of the current intensity I which it receives.

As may be noted from the description of the compression device described above, this device, the moving element of which consists of the floating membrane 2, has no other moving parts generating mechanical friction, the only friction being that which occurs in the material of the floating membrane 2 and the springy arms 17, 18, but this friction is included in the constants of the device and has a very low value.

Furthermore, since the compression device comprises only a single floating membrane, the moving mass is reduced to a minimum, as is the noise emission. The floating membrane 2 requires a driving coil 14 of small height in the gap E, so that the distribution of the force exerted on the floating membrane 2 is uniform whatever the position of this floating membrane 2. It is necessary that $h_{gap} \geq travel_{coil} = h_{coil}$.

A coil 14 of low height also has the advantage of decreasing its resistance, and therefore the Joule heating losses ($I^2R$), thus improving the overall efficiency of the compression device.

By virtue of the fact that, with such a compression device, the only variable, for a given reference pressure of the pressurized air supplied to the outlet duct 13, is the demanded flow rate which depends on the instantaneous suction, therefore on the low pressure generated by the patient, it becomes quite possible to control the respiratory assistance apparatus by an open-loop system, which makes it possible to reduce the response time compared to a regulating system with feedback, by between 5 and 30 times.

The flow rate can advantageously be measured by detecting the position of the floating membrane 2, the surface of which may be reflecting or may be combined with a reflecting element, with the help of the light-emitting diode 24 which sends a light spot having a particular angle of incidence, for example 60°, onto the reflecting surface, the photodiode 25 receiving the light reflected by the floating membrane 2 as a function of the position of this floating membrane 2. Preferably, the amplitude of the floating membrane 2 is fixed.

The air pressure at the outlet of the compression device must be:

$$P_{aw} = \Delta P_{ETT} + P_e$$
$$= R \cdot \dot{V}(t) + R_2 \cdot \dot{V}^2(t) + P_e$$

where:
$P_{aw}$=outlet pressure of air from the compression device
$P_e$=endotracheal reference pressure
$P_{ETT}$=pressure drop in the nozzle of the respiratory assistance apparatus, mainly the intubation cannula V(t)=y(t)·S
S=effective surface area of membrane hence: $\dot{V}(t) = \dot{y}(t) \cdot S$ Newton's law; applied to the moving element, that is the driving coil 14, the floating membrane 2 and the springy arms 17, 18, gives:

$$\Sigma F = m \cdot a = m \cdot \ddot{y}(t)$$

$$P_{awS}(t) \cdot S + BII(t) + k \cdot y(t) + \eta \cdot \dot{y}(t) = m\ddot{y}(t)$$

by inserting $P_{aw} = R\dot{V}(t) + R_2\dot{V}^2 + P_e$
where:
  η=internal friction of floating membrane
  k=spring constant of the system
we obtain:

$$I(t) = -\frac{1}{Bl}\left[SR\dot{V}(t) + SR_2\dot{V}^2(t) + SP_e + k \cdot y(t) + \eta \cdot \dot{y}(t) - m \cdot \ddot{y}(t)\right]$$

in which equation:

$$y(t) = \frac{V(t)}{S}$$

$$\dot{y} = \frac{\dot{V}}{S}$$

$$\ddot{y} = \frac{\ddot{V}}{S}$$

that is:

$$I(t) = -\frac{1}{Bl}\left[\left(SR + \frac{\eta}{S}\right)\dot{V}(t) + SR_2\dot{V}^2(t) + \frac{k}{S}V(t) - m\frac{\ddot{V}(t)}{S} + SP_e\right]$$

Apart from:

$$I(P_e) = \frac{S \cdot P_e}{Bl},$$

the other terms of the equation are corrections depending on the flow rate, making it possible to keep $P_e$ constant whatever the value of t and $\dot{V}(t)$.

The current in the driving coil 14 can be continuously calculated either by an analog computer or, advantageously, using a digital signal processing unit (DSP) or a microcontroller in which:

B,l,S,η,k,m are known construction constants of the respirator.

R,$R_2$ are constants dependent on the cannula introduced into the patient's trachea. These constants are entered into the regulating system by means of a keyboard and are determined by preliminary calibration before ventilating the patient.

V(t),$\dot{V}$(t),$\ddot{V}$(t) are calculated on the basis of V(t)=y(t)·S where y(t) is measured by the photodiode 25.

$P_e$ is the desired endotracheal reference pressure which is input into the regulating system by the practitioner using a keyboard.

The instantaneous flow rate and the instantaneous frequency of the compression device described vary depending on demand from the patient.

Figure 3:
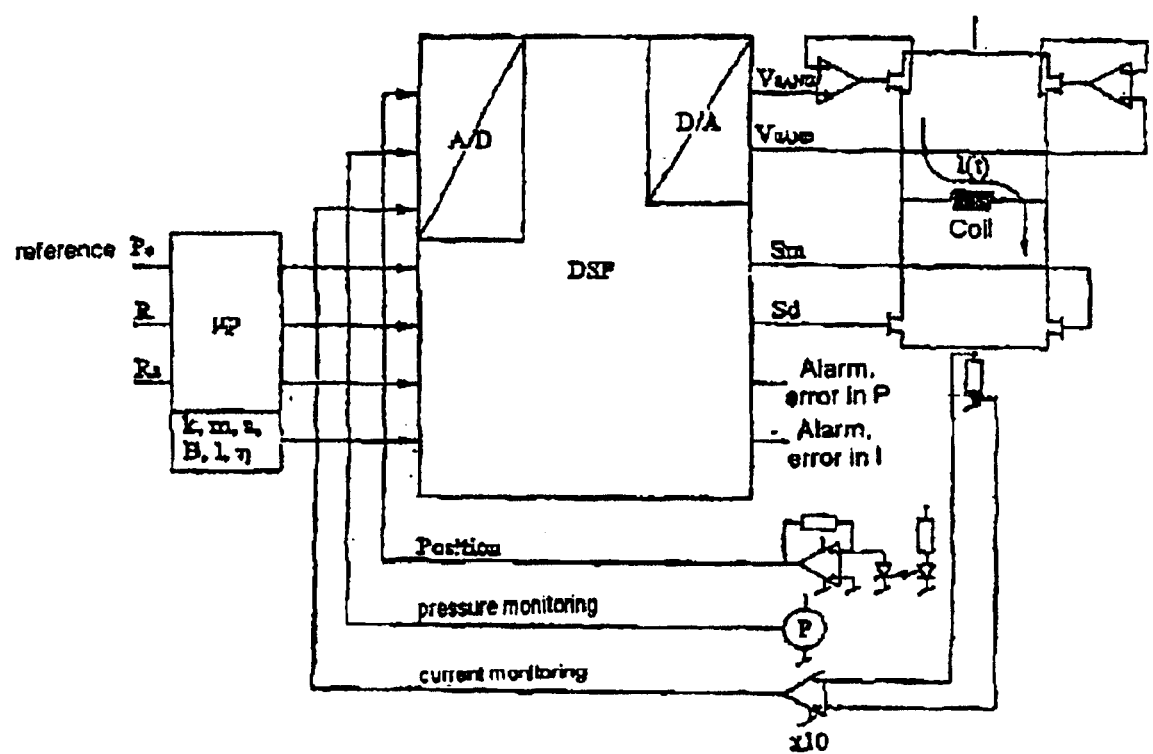
FIG. 3 is a block diagram of the system for regulating the respirator.

As illustrated in FIG. 3, the regulating system for implementing the method which is the subject of the invention preferably comprises a digital signal processing unit DSP, the inputs of which are connected so as to receive the various values involved in calculating the intensity of the current supplying the driving coil 14. The values introduced into the DSP comprise, on the one hand, digital values, that is the constants k,η,m,S,B,l, the values R, $R_2$, $P_e$, and on the other hand, analog values, those supplied by the photodiode 25, that from measuring the supply current as a function of time $I_{mes}(t)$ and that from a safety pressure sensor $P_s$, the role of which is to trigger an alarm if the measured pressure moved away from the reference value.

These analog values are input into an analog-digital converter A/D of the DSP unit and the current supplying the driving coil 14 is generated by a bidirectional power amplifier Amp supplied with voltage of 12 or 24 V, the inputs of which are connected to the output of a digital-analog converter D/A of the DSP unit, in order to modulate the intensity of the supply current as a function of the value calculated by the DSP unit. The latter has another two outputs $S_m$, $S_d$ which determine the direction in which the current passes through the driving coil 14 and therefore the direction of displacement of this coil 14 in the gap between the soft iron core 21 and the soft iron yoke 22 as a function of its position, thus determining the amplitude of its displacement in this gap and in some way playing the role of "electronic stops" between which the floating membrane 2 is displaced.

What is claimed is:

1. A method of regulating pressure in open-loop mode for a respiratory assistance apparatus having a compression chamber which is divided into two compartments, each compartment being connected to an air or respiratory gas intake and to a compressed air outlet by a resilient floating membrane, this floating membrane is exclusively guided by fastening its periphery to the wall of the said chamber, a driving coil is fastened to the center of said floating membrane, this driving coil is placed in a gap which is oriented in the direction in which said floating membrane is deformed, the instantaneous flow rate of air exiting by said outlet is measured and said driving coil is supplied by continuously calculating the instantaneous intensity and the direction of the supply current as a function of the reference pressure of the insufflated air, said instantaneous flow rate and the constants of said apparatus.

2. The method as claimed in claim 1, wherein said instantaneous flow rate is measured by continuously detecting the variation of axial position of said floating membrane as a function of time.

3. A respiratory assistance apparatus, comprising: a compression chamber, a resilient floating membrane dividing this compression chamber into two compartments, each compartment being connected to an air or respiratory gas intake and to a compressed gas outlet, exclusively guided by its periphery fastened to the wall of said chamber, a driving coil fastened to the center of said membrane, a gap in which said driving coil is positioned, this gap being oriented in the direction in which said floating membrane is deformed, means to measure the flow rate of said compression chamber and a digital signal processing unit (DSP) to calculate the instantaneous intensity of the supply current in said driving coil.

4. The apparatus as claimed in claim 3, wherein said membrane is combined with at least two electrically conducting flexible guiding elements for connecting said driving coil to a supply source controlled by said digital signal processing unit.

5. The apparatus as claimed in claim 4, wherein said guiding and connection means comprise at least two arms, made of Cu—Be alloy, placed symmetrically with respect to the center of said membrane.

6. The device as claimed in claim 4, wherein said driving coil and said gap form an electrodynamic motor.

7. The device as claimed in claim 5, wherein said driving coil and said gap form an electrodynamic motor.

8. The device as claimed in claim 4, wherein said resilient floating membrane is fastened to the wall of said chamber with a diametral pretension of 3 to 8% elongation.

9. The device as claimed in claim 5, wherein said resilient floating membrane is fastened to the wall of said chamber with a diametral pretension of 3 to 8% elongation.

10. The device as claimed in claim 3, wherein said driving coil and said gap form an electrodynamic motor.

11. The device as claimed in claim 3, wherein said resilient floating membrane is fastened to the wall of said chamber with a diametral pretension of 3 to 8% elongation.

12. A respiratory assistance apparatus, comprising: a compression chamber, a resilient floating membrane dividing this compression chamber into two compartments, each compartment being connected to an air or respiratory gas intake and to a compressed gas outlet, guided by its periphery fastened to the wall of said chamber, a driving coil fastened to the center of said membrane, a gap in which said driving coil is positioned, this gap being oriented in the direction in which said floating membrane is deformed, means to measure the flow rate of said compression chamber and a digital signal processing unit (DSP) to calculate the instantaneous intensity of the supply current in said driving coil; wherein said membrane is combined with at least two electrically conducting flexible guiding elements for connecting said driving coil to a supply source controlled by said digital signal processing unit.

13. The apparatus as claimed in claim 12, wherein said guiding and connection means comprise at least two arms, made of Cu—Be alloy, placed symmetrically with respect to the center of said membrane.

14. The apparatus as claim 13, wherein said driving coil and said gap form an electrodynamic motor.

15. The apparatus as claimed in claim 13, wherein said resilient floating membrane is fastened to the wall of said chamber with a diametral pretension of 3 to 8% elongation.

16. The apparatus as claimed in claim 13, wherein said driving coil and said gap form an electrodynamic motor.

17. The apparatus as claimed in claim 12, wherein said resilient floating membrane is fastened to the wall of said chamber with a diametral pretension of 3 to 8% elongation.

* * * * *